United States Patent [19]
Crawford

[11] Patent Number: 5,944,654
[45] Date of Patent: Aug. 31, 1999

[54] ENDOSCOPE WITH REPLACEABLE IRRIGATION TUBE

[75] Inventor: John O. Crawford, Hopkinton, Mass.

[73] Assignee: Vista Medical Technologies, Inc., Carlsbad, Calif.

[21] Appl. No.: 08/748,775

[22] Filed: Nov. 14, 1996

[51] Int. Cl.⁶ ................................................ A61B 1/015
[52] U.S. Cl. ...................... 600/157; 600/128; 600/130; 600/156
[58] Field of Search .................... 600/128, 130, 600/136, 153, 156, 157; 604/283, 264

[56] References Cited

U.S. PATENT DOCUMENTS

| | | | |
|---|---|---|---|
| Re. 34,110 | 10/1992 | Opie et al. .............................. | 600/128 |
| 4,616,631 | 10/1986 | Takahashi ............................ | 600/158 X |
| 4,826,280 | 5/1989 | Hiramoto ............................. | 600/130 X |
| 4,947,827 | 8/1990 | Opie et al. ............................ | 600/153 X |
| 5,154,164 | 10/1992 | Chikama .............................. | 600/128 X |
| 5,257,617 | 11/1993 | Takahashi ............................ | 600/128 X |
| 5,630,795 | 5/1997 | Kuramoto et al. ................... | 600/153 X |
| 5,667,472 | 9/1997 | Finn et al. ............................ | 600/160 |

FOREIGN PATENT DOCUMENTS

WO9104703   4/1991   WIPO .

*Primary Examiner*—John P. Leubecker
*Attorney, Agent, or Firm*—Pandiscio & Pandiscio

[57] ABSTRACT

An endoscope apparatus includes a handle assembly and an outer tube having a distal end and a proximal end, the latter being fixed to the handle assembly. The outer tube is provided with a groove in an outermost surface of the outer tube and extending lengthwise of the outer tube. The apparatus further includes an irrigation tube for disposal in the groove for conducting fluid in a direction from the proximal end to the distal end.

2 Claims, 4 Drawing Sheets

ENDOSCOPE WITH REPLACEABLE IRRIGATION TUBE

BACKGROUND OF THE INVENTION

1. Field of the Invention

This invention relates to endoscopes and is directed more particularly to an endoscope apparatus having means for conducting irrigation fluids to the distal end of the apparatus.

2. Description of the Prior Art

Endoscopes, which are instruments used to inspect cavities or openings, have found a great number of applications in medicine and other technologies. In the field of medicine, the use of endoscopes permits inspection of organs, or other biological specimens, for the purpose of inspecting a surgical site, sampling tissue, and/or facilitating the manipulation of other surgical instruments, usually with the objective of avoiding invasive and traumatizing surgical procedures.

Older conventional endoscopes used in medicine have an objective lens unit at their distal (forward) ends which transmits an image of the area forward of the objective lens unit to the proximal (rear) end of the endoscope for viewing in an eye-piece, the image being transmitted to the eye-piece via an image forwarding means in the form of a relay lens set or an optical fiber bundle unit. In more recent years, in place of the eye-piece and at least part of the image forwarding means, it has been preferred to provide a small size solid state video imaging device, such as one constituting a CCD chip, in the imaging plane of the objective lens, and applying the output of that video imaging device via a suitable electronic transmission system to a video monitor for viewing by a user. With both types of image transmitting and viewing arrangements, a surgeon can view the displayed image and use the information conveyed by that image to manipulate the endoscope and other surgical instruments that have been inserted into the patient via another incision or opening in the patient's body. In the case of endoscopes that incorporate a solid state video imaging device, the image seen by the objective lens unit can be observed in the display provided by the video monitor with or without magnification.

In U.S. patent application Ser. No. 08/319, 886, filed Oct. 7, 1994, now U.S. Pat. No. 5,582,576, in the names of Koichiro Hori, et al., there are shown and described optical, electronic and mechanical components of a contemporary endoscope.

It has been found to be beneficial to provide in or on endoscopes an irrigation tube for the purpose of providing fluid (liquid or gas, including air) to the distal end of the endoscope for (1) cleaning a window of the endoscope, and/or (2) irrigating an endoscopic site.

In the past, the need for irrigation has produced endoscope modifications not entirely successful. For example, some prior art devices have been provided with an external sheath around the outer surface of the endoscope, with the irrigant flowable between the endoscope and the surrounding sheath. However, a critical requirement of surgical endoscopes is that the maximum cross-sectional dimension of the endoscope be kept quite small, in keeping with the objective of avoiding invasive and traumatizing surgical procedures. The addition of an external sheath necessarily results in an increase in diameter of the endoscope.

In other prior art devices, a permanent external channel has been provided, which results in a local increase in diameter of the endoscope and, further, renders the endoscope difficult to use in conjunction with trocar sheaths of round cross-section.

In still other prior art devices, a small diameter irrigation tube has been integrated into the internal structure of the endoscope. The demands placed on the endoscope internal space necessitate very small irrigation tube diameters, which, because of their position and size, make sterilization of the irrigation tube very difficult.

Thus, in spite of previous attempts to solve the problem, there remains a need for an irrigation tube arrangement which requires little or no internal space, does not substantially enlarge the diameter of the endoscope, and is relatively easy to sterilize.

SUMMARY OF THE INVENTION

Accordingly, an object of the invention is to provide an endoscope apparatus having irrigation means which requires little or no internal space, does not substantially enlarge the diameter of the endoscope, and which is so configured and arranged as to render the sterilization thereof relatively easy.

With the above and other objects in view, as will hereinafter appear, a feature of the invention is the provision of an endoscope apparatus comprising a handle assembly, and an outer tube having a distal end and a proximal end, the proximal end being fixed to the handle assembly. The outer tube is provided with a groove in an outermost surface thereof and extending lengthwise thereof. The apparatus further includes an irrigation tube for disposal in the groove for conducting fluid in a direction from the proximal end to the distal end.

The above and other features of the invention, including various novel details of construction and combinations of parts, will now be more particularly described with reference to the accompanying drawings and pointed out in the claims. It will be understood that the particular devices embodying the invention are shown by way of illustration only and not as limitations of the invention. The principles and features of this invention may be employed in various and numerous embodiments without departing from the scope of the invention.

BRIEF DESCRIPTION OF THE DRAWINGS

Reference is made to the accompanying drawings in which are shown illustrative embodiments of the invention, from which its novel features and advantages will be apparent.

In the drawings.

Figure 1:
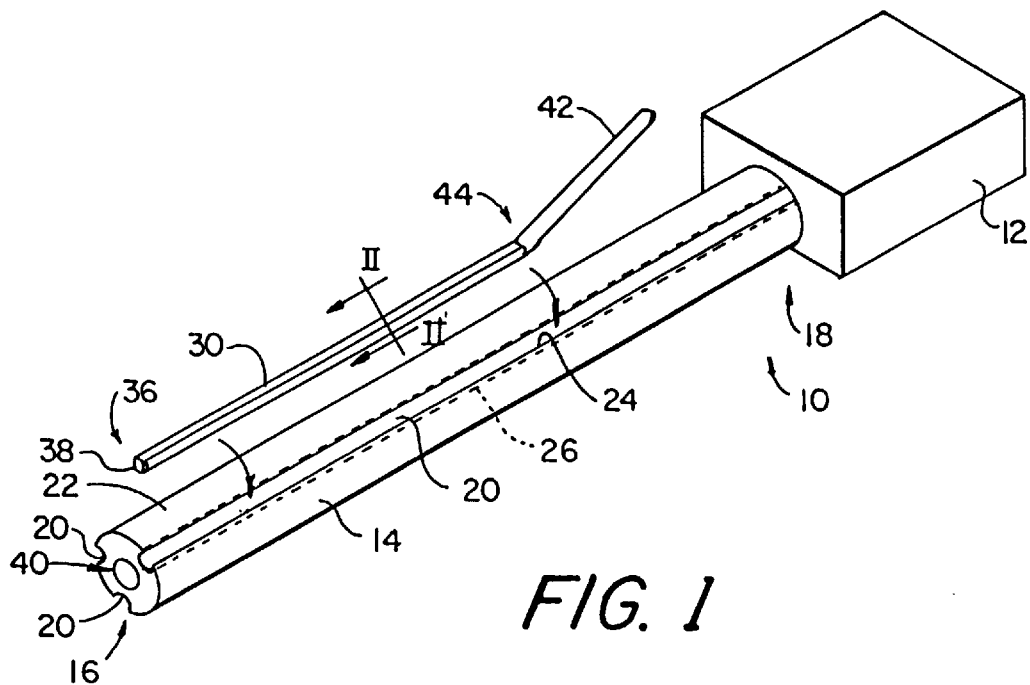
FIG. 1 is an exploded perspective view of one form of endoscope apparatus illustrative of an embodiment of the invention.

For convenience of illustration and also to better indicate the nature of the novel features of the invention, the relative sizes of the several components are not necessarily to scale in the drawings.

DESCRIPTION OF THE PREFERRED EMBODIMENTS

Endoscopes may be provided with a pair of flexible or rigid tubes, one inside of the other, with the various optical, electronic and mechanical components required to form a functioning endoscope being mounted inside the inner tube and, preferably but not necessarily, light-transmitting means disposed between the inner and outer tubes. Alternatively, endoscopes may consist of a single flexible or rigid tube containing various optical, electronic and mechanical components required to form a functioning endoscope. Therefore, as used herein, the term "outer tube" is intended to refer to either the outermost tube of a plurality of tubes or the single tube of a single tube endoscope.

Referring to FIG. 1, it will be seen that an illustrative embodiment of the inventive endoscope apparatus 10 includes a handle assembly 12 and an outer tube 14 having a distal end 16 and a proximal end 18, with the latter end being fixed to handle assembly 12. The optical, electronic and mechanical components of the endoscope, which are contained within outer tube 14 and handle assembly 12, may take various forms and, for example, may be as disclosed in the aforementioned patent application. A detailed description of those components is not provided herein inasmuch as they form no part of the present invention and the invention may be practiced with various forms of endoscopes.

Referring again to FIG. 1, it will be seen that outer tube 14 is provided with at least one groove 20 in an outermost surface 22 of outer tube 14 and extending lengthwise of outer tube 14. The endoscope apparatus 10 further includes an irrigation tube 30 for disposal in groove 20 for conducting fluid (liquid and/or gas, including air, singularly or in combination) in a direction from proximal end 18 of outer tube 14 to distal end 16 of outer tube 14.

Figure 2:
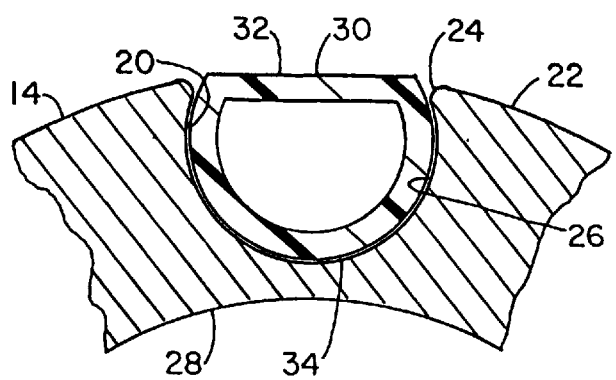
FIG. 2 is a partial sectional view taken along line 11—11 of FIG. 1, modified to show the exploded components together.
Figure 3:
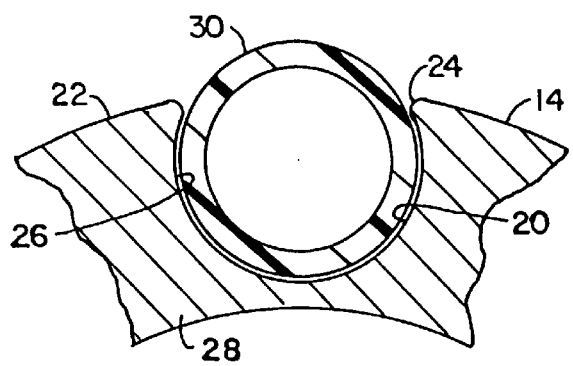
FIG. 3 is similar to FIG. 2, but illustrative of an alternative embodiment of the invention.

Referring to FIGS. 2 and 3, it will be seen that groove 20 in tube 14 is generally circular in cross section and is provided with a first portion 24 at outermost surface 22 of outer tube 14 which is narrower than a second portion 26 of groove 20 which is removed from outermost surface 22 of outer tube 14.

Still referring to FIG. 2, it will be seen that in one embodiment the irrigation tube 30 is substantially D-shaped with a flat portion 32 of the tube 30 adapted for disposition at the narrower first portion 24 of groove 20, and a rounded portion 34 of tube 30 adapted for disposition in second portion 26 of groove 20. The disposition of flat portion 32 of irrigation tube 30 in groove narrow first portion 24 insures that tube 30 is confined entirely to groove 20 and to the circumference of outermost surface 22 of outer tube 14. That is, in this embodiment no part of irrigation tube 30 extends outwardly beyond outermost surface 22 of outer tube 14.

Figure 6:
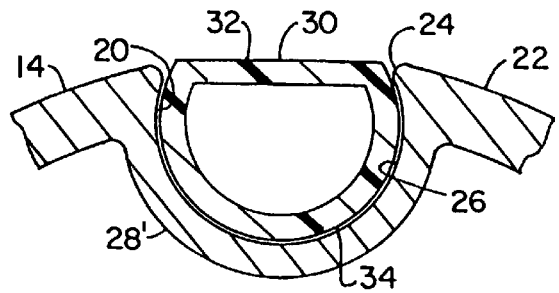
FIG. 6 is similar to FIG. 2, but illustrative of another alternative embodiment of the invention.

As shown in FIG. 2, in some endoscopes, notably those comprising a single tube, the wall 28 of tube 14 may be of sufficient thickness to have groove 20 machined therein. In such instances, the groove 20 and irrigation tube 30 require no space interiorly of the outer tube 14. In other endoscopes, notably those having two concentric tubes, the wall 28' of tube 14 may be thinner than the depth of groove 20 and in such instances, as shown in FIG. 6, the wall 28' of outer tube 14 is configured to form groove 20. The latter embodiment requires a limited amount of interior space, which is more than offset by the use of the thinner outer tube wall 28' (if the outside diameter of outer tube 14 remains constant).

Figure 7:
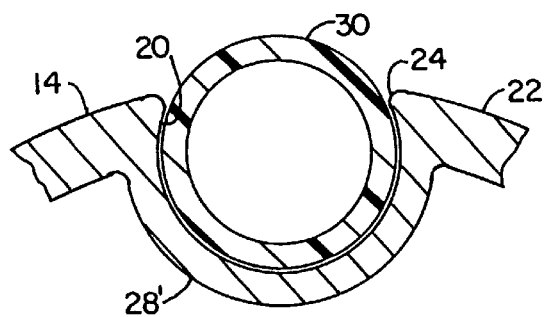
FIG. 7 is similar to FIG. 3, but illustrative of still another alternative embodiment of the invention.

Referring again to FIG. 3 and to FIG. 7, it will be seen that in an alternative embodiment the irrigation tube 30 is round in configuration and may extend slightly beyond the outermost surface 22 of outer tube 14. The tube 30 is sufficiently flexible that when used with a cannula apparatus 50 (FIG. 4), the irrigation tube 30 is pressed inwardly into the confines of groove 20 so as to assume a substantially "D" configuration.

The irrigation tube 30 may be of a material, such as an elastomeric material, which is sufficiently elastic and resilient to allow irrigation tube 30 to be inserted into groove 20 in a direction radially inwardly of outer tube 14. More specifically, irrigation tube 30 may be sufficiently deformable to pass through groove first portion 24 and enter groove second portion 26 in a "snap-in" manner. Alternatively, the irrigation tube 30 may have sufficient rigidity and structural strength to permit moving the irrigation tube 30 axially into and through the groove 20. One irrigation tube found to be acceptable for axial insertion is of a 60 durometer Teflon fluoroelastomer having an outside diameter of 0.040 inch and an inside diameter of 0.019 inch.

Figure 8:
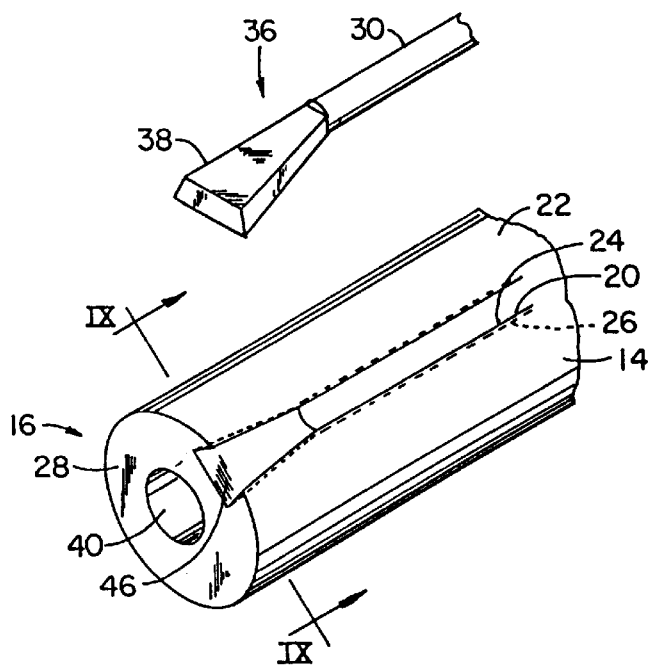
FIG. 8 is an exploded perspective view of an end portion of an endoscope apparatus illustrating a deflector portion of the invention.
Figure 9:
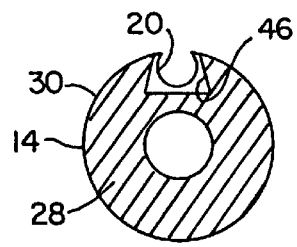
FIG. 9 is a sectional view taken along line IX—IX of FIG. 8.

The irrigation tube 30 may be provided, at a distal end 36 thereof, with a deflector 38 (FIG. 8) that extends beyond the distal end face of endoscope outer tube 14 a short distance and is angled inwardly toward the axis of that tube, whereby to direct fluid inwardly toward a window 40 that closes off the distal end 16 of outer tube 14, so as to irrigate and clean the window. The groove 20 may be provided with an enlarged distal end portion 46 for snugly receiving the deflector 38 and to guide the irrigation tube 30 into the groove 20 when axial insertion of the irrigation tube 30 is desired. The irrigation tube 30 may be further provided with a flexible conduit 42 (FIG. 1), attached to a proximal end 44 of irrigation tube 30, that extends away from tube 30 for connection to a fluid source and/or valve means (not shown).

In practice, the irrigation tubes 30 preferably are disposable and are prepackaged in sterile condition ready to be inserted into groove 20. The groove 20, being open on one side, is readily sterilized and maintained in a sterile condition. In preparation for use, a pre-packaged irrigation tube 30 is selected having an appropriate deflector 38 for providing appropriate dispersion of irrigant to the window 40 and/or to the endoscopic site. The tube is removed from its sterile packaging and then pressed against groove 20, generally radially inwardly, until the tube passes through first groove portion 24 and "snaps into" second groove portion 26. Alternatively, the irrigation tube 30 is inserted in the distal end of groove 20, proximal end first, and then slid axially along groove 20 into place, with the deflector 38 coming to rest in the enlarged end portion 46 of the groove 20. The conduit 42 is then connected to the fluid source and/or valve means (not shown) and the apparatus 10 is ready for use. The narrowed first groove portion 24 retains irrigation tube 30 in groove 20. After use, irrigation tube 30 may be stripped from groove 20, radially or axially, And disposed of. The open groove 20 is again accessible for sterilization.

Figure 10:
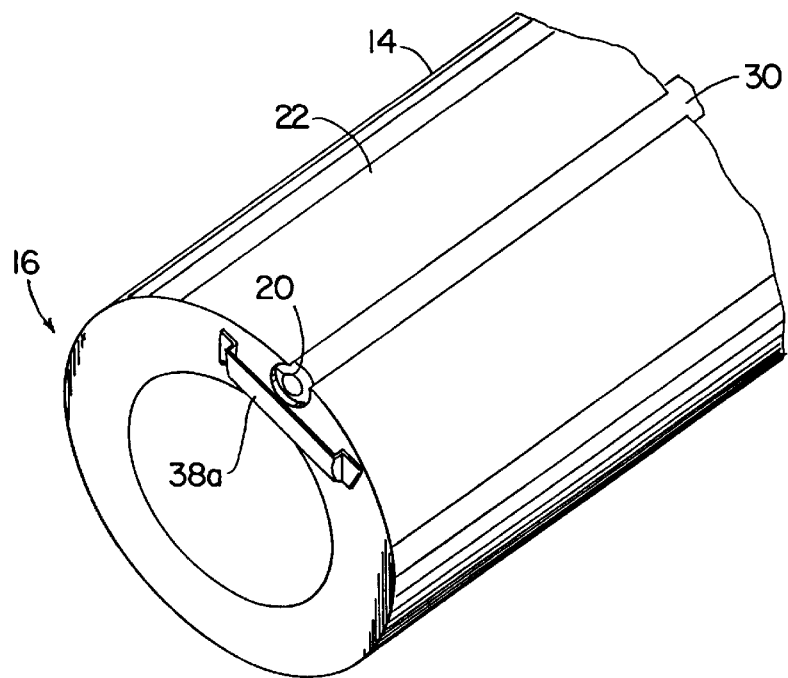
FIG. 10 is a perspective view of an end portion of an endoscope apparatus illustrating an alternative deflector portion of the invention.
Figure 11:
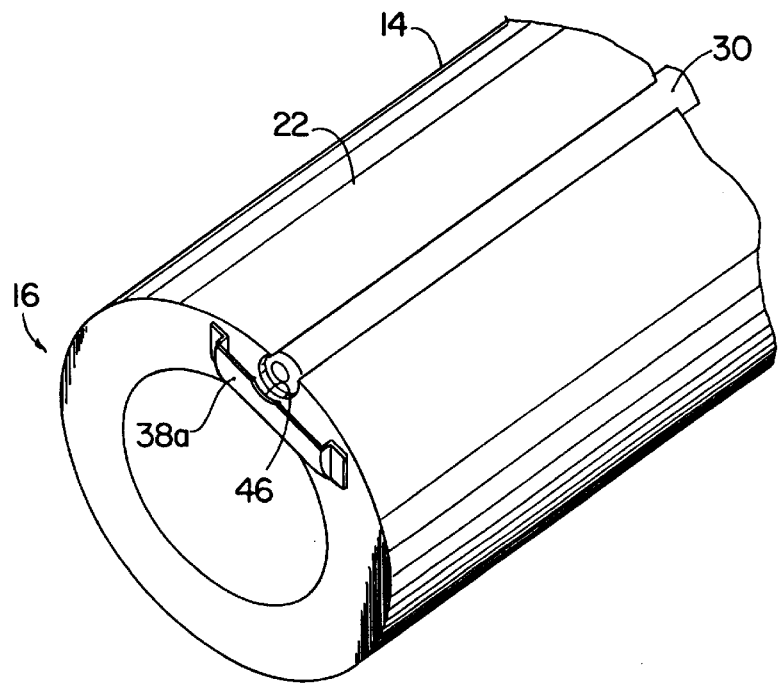
FIG. 11 is similar to FIG. 10 but illustrative of another alternative embodiment of deflector portion.

Referring to FIG. 10, it will be seen that in an alternative embodiment the deflector 38a is mounted on the distal end 16 of outer tube 14 in partial alignment with groove 20 so as to intercept and direct at least some of the fluid emitted from tube 30 toward the distal end of tube 14. In this embodiment, tube 30 is "snapped" radially into groove 20. In FIG. 11, there is shown a similar arrangement accommodating axial insertion of tube 30 into groove 20 at the distal end of groove 20, by provision, in the deflector 38b, of a recess 48 permitting axial passage of tube 30 therethrough. Recess 48 is located so that at least some of the discharged fluid impacts the deflector and is directed at the distal end of tube 14.

Referring to FIG. 1, it will be seen that outer tube 14 may be provided with a plurality of grooves 20, each adapted to receive an irrigation tube of the type described above. It will be apparent that provision of a plurality of grooves and irrigation tubes provides selectivity to an operator as to the type of fluid desired by the operator at a given time, depending upon the fluid sources available and the manner in which the conduits 42 are connected to the fluid sources (not shown).

Figure 4:
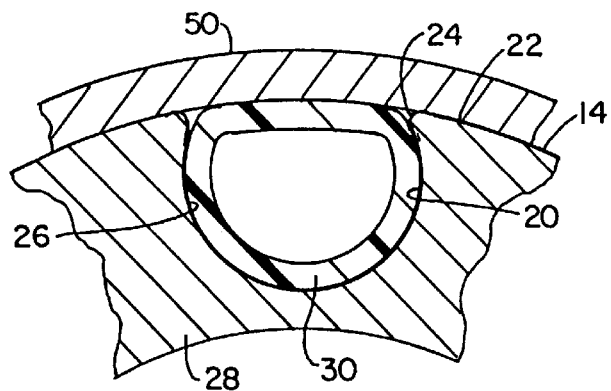
FIG. 4 is a sectional view illustrative of the embodiment of FIG. 3 in combination with a cannula apparatus.
Figure 5:
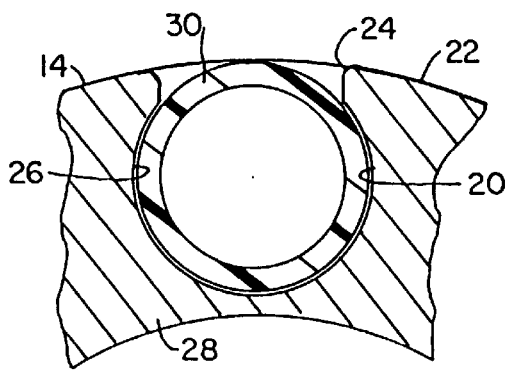
FIG. 5 is similar to FIG. 3, but illustrative of an alternative embodiment of the invention.

There is thus provided an endoscope apparatus having irrigation means which take up little (FIGS. 6 and 7 embodiments) or no (FIGS. 2–5 embodiments) internal space within the outer tube. There is further provided an irrigation tube arrangement which is confined to the outer boundary of the endoscope outer tube (FIGS. 2, 5 and 6) and therefore does not add to the diameter thereof, either circumferentially or locally; or, which extends minimally beyond the endoscope outer boundary, but by so little as to be pressed back to within the endoscope circumference when in use (FIGS. 3, 4 and 7). Finally, there is provided an irrigation arrangement which is readily amenable to being sterilized and/or being maintained in a sterile condition.

It is to be understood that the present invention is by no means limited to the particular constructions herein disclosed and/or shown in the drawings, but also comprises other modifications or equivalents within the scope of the claims.

What is claimed is:

1. An endoscope apparatus comprising:

a handle assembly;

an endoscope tube having a distal end and a proximal end, said proximal end being fixed to said handle assembly, said endoscope tube having a groove in an outermost surface thereof that extends lengthwise between said distal and proximal ends, said groove having in cross-section a first relatively narrow portion at said outermost surface and a second relatively wide portion at a point removed from said first relatively narrow portion;

an irrigation tube that is made of a flexible, resilient material and is formed with an outer diameter greater than the width of said first relatively narrow portion of said groove, said irrigation tube being removably disposed in and extending lengthwise of said groove, with at least a major portion of said irrigation tube residing in said relatively wide portion of said groove and being gripped by said endoscope tube, and said irrigation tube having a distal end with a discharge opening adjacent said distal end of said endoscope tube; and a deflector fixed to said distal end of said endoscope tube and at least in part aligned with said groove, so as to deflect fluid discharged from said discharge opening, said deflector being provided with a recess to facilitate axial insertion of said irrigation tube into said groove.

2. An endoscope apparatus comprising:

a handle;

an endoscope tube having a distal end and a proximal end, with said distal end having an end face and said proximal end being fixed to said handle, said endoscope tube having a groove in an outermost surface thereof that extends lengthwise between said distal and proximal ends, said groove having in cross-section a first relatively narrow portion at said outermost surface and a second relatively wide portion at a point removed from said first relatively narrow portion;

an irrigation tube that is made of a flexible, resilient material and is formed with an outer diameter greater than the width of said first relatively narrow portion of said groove, said irrigation tube being removably disposed in and extending lengthwise of said groove, with at least a major portion of said irrigation tube residing in said relatively wide portion of said groove and being gripped by said endoscope tube, and said irrigation tube having a distal end with a discharge opening adjacent said distal end of said endoscope tube; and a deflector attached to said distal end of said irrigation tube with said deflector extending beyond the distal end of said irrigation tube and angled inwardly toward the longitudinal axis of said endoscope tube, whereby to direct fluid passing out of said discharge opening toward said end face of said distal end of said endoscope tube;

said groove having an enlarged portion at said distal end of said endoscope tube and at least a portion of said deflector being disposed in said enlarged portion of said groove.

* * * * *